United States Patent [19]

MacGregor

[11] Patent Number: 4,994,071
[45] Date of Patent: Feb. 19, 1991

[54] BIFURCATING STENT APPARATUS AND METHOD

[75] Inventor: David C. MacGregor, Miami, Fla.

[73] Assignee: Cordis Corporation, Miami, Fla.

[21] Appl. No.: 354,799

[22] Filed: May 22, 1989

[51] Int. Cl.$^5$ .................... A61M 29/00; A61F 2/06
[52] U.S. Cl. ............................ 606/194; 606/192
[58] Field of Search ............... 606/191, 192, 198, 200, 606/194, 96, 151, 153; 623/1, 12

[56] References Cited

U.S. PATENT DOCUMENTS

| | | | |
|---|---|---|---|
| 3,993,078 | 11/1976 | Bergentz et al. | 606/156 |
| 4,501,264 | 2/1985 | Rockey | 606/192 X |
| 4,733,665 | 3/1988 | Palmaz | 606/191 X |
| 4,795,465 | 1/1989 | Marten | 623/12 X |
| 4,830,003 | 5/1989 | Wolff et al. | 606/191 |
| 4,842,575 | 6/1989 | Hoffman, Jr. et al. | 623/1 X |
| 4,856,516 | 8/1989 | Hillstead | 604/96 X |
| 4,913,141 | 4/1990 | Hillstead | 606/194 X |

Primary Examiner—Robert A. Hafer
Assistant Examiner—Kevin G. Rooney
Attorney, Agent, or Firm—Watts, Hoffmann, Fisher & Heinke Co.

[57] ABSTRACT

A bifurcating stent for insertion into a bifurcating vessel such as a blood vessel. The stent can be expanded from an insertion configuration to an implanted configuration by the application of radially outward forces against a series of interconnected wire loops that make up the stent. The preferred and disclosed method of stent implantation is accomplished with the use of a balloon catheter that expands the stent into contact with inner walls of the vessel. The balloon is then deflated and withdrawn from the vessel, leaving the stent implanted within the vessel.

16 Claims, 3 Drawing Sheets

BIFURCATING STENT APPARATUS AND METHOD

TECHNICAL FIELD

The present invention relates to an endoprosthesis device for implantation within a body vessel, typically a blood vessel.

BACKGROUND ART

A type of endoprosthesis device, commonly referred to as a stent, is placed or implanted within a blood vessel for treating occlusions, stenoses, or aneurysms in the blood vessel. These devices are implanted within the vascular system to reinforce collapsing, partially occluded, weakened, or abnormally dilated sections of the blood vessel. Stents also have been successfully implanted in the urinary tract or the bile duct to reinforce those body vessels.

One of the drawbacks of conventional stents is that they are produced in a straight tubular configuration. The use of such a stent to treat disease at or near a branch or bifurcation of a blood vessel runs the risk of compromising the degree of patency of the primary vessel and/or its branches or bifurcation. This may occur as a result of several problems such as displacing diseased tissue, vessel spasm, dissection with or without intimal flaps, thrombosis, and embolism.

One common procedure for implanting the endoprosthesis or stent is to first open the region of the vessel with a balloon catheter and then place the stent in a position that bridges the weakened portion of the vessel.

Prior art patents refer to the construction and design of both the stent as well as the apparatus for positioning the stent within the vessel. One representative patent is U.S. Pat. No. 4,140,126 to Chaudhury which issued Feb. 20, 1979. This patent discloses a technique for positioning an elongated cylindrical stent at a region of an aneurysm to avoid catastrophic failure of the blood vessel wall. The '126 patent discloses a cylinder that expands to its implanted configuration after insertion with the aid of a catheter A second prior art patent to Dotter U.S. Pat. No. 4,503,569 which issued Mar. 12, 1985 discloses a spring stent which expands to an implanted configuration with a change in temperature. The spring stent is implanted in a coiled orientation and heated to cause the spring to expand.

U.S. Pat. No. 4,733,665 to Palmaz which issued Mar. 29, 1988 discloses a number of stent configurations for implantation with the aid of a catheter. The catheter includes a mechanism for mounting and retaining the vascular prosthesis or stent, preferably on an inflatable portion of the catheter The stent is implanted by positioning it within the blood vessel and monitoring its position on a viewing monitor. Once the stent is properly positioned, the catheter is expanded and the stent separated from the catheter body. The catheter can then be withdrawn from the subject, leaving the stent in place within the blood vessel.

U.S. Pat. No. 4,413,989 to Schjeldahl et al. which issued Nov. 8, 1983 discloses a variety of balloon catheter constructions. FIG. 5 of this patent discloses a bifurcating expander for insertion into diverging branches of a subject blood vessel.

U.S. Pat. No. 3,993,078 to Bergentz et al. discloses an insert for use in vascular surgery. The embodiment of this insert disclosed in FIG. 2 forms a "Y" tube. A distinguishing feature of the inserts disclosed in this patent is the ability to take apart the insert by pulling a free end of a thread that forms the insert. This insert is surgically placed within a subject and no mention is made concerning the non-surgical placement of such an insert within a vessel.

U.S. patent application Ser. No. 240,000 entitled "Radially Expandable Endoprosthesis and the Like" discloses a generally cylindrical stent formed from a wire that is bent into a series of tight bends and then spirally wound about a cylindrical mandrel to form the stent. If a radially outward force is applied to the stent the sharp bends in the wire tend to straighten and the stent diameter enlarges. One technique for implanting this stent uses a deflated balloon catheter to position the stent within a vessel. Once the stent is properly positioned the balloon is inflated to press the stent against the inner wall linings of the vessel. The balloon is then deflated and withdrawn from the vessel, leaving the stent in place.

DISCLOSURE OF THE INVENTION

The present invention concerns a stent and more particularly a bifurcating stent for insertion into a branching vessel of a subject. A stent constructed in accordance with the invention includes structure that defines a first flow path for fluid to flow through the stent. More particularly, a series of interconnected loops extend axially along and bound this first fluid flow path.

Additional structure, preferably constructed using a second series of interconnected loops, defines a second branching fluid flow path. A flexible interconnection joins the structure that defines the first and second flow paths. By proper bending of the flexible interconnection the first and second fluid flow paths can be made to conform to a shape of the vessel into which the bifurcating stent is inserted.

The bifurcating stent is constructed from a material that allows the stent to be expanded from an initial shape which can be inserted into a branching vessel to an expanded shape fixed within the branching vessel. A balloon catheter is preferably used to expand the stent by application of outward forces against the series of loops that make up the stent. To deposit the bifurcating stent within the subject, the balloon is expanded to bring the stent into contact with the inner walls of the vessel and then deflated, leaving the stent in place.

A preferred use for a bifurcating stent constructed in accordance with the present invention is for insertion into a branching blood vessel. A stent constructed in accordance with the present invention is typically intended for use in the coronary vasculature (the right, left common, left anterior descending, and circumflex coronary arteries and their branches) and the peripheral vasculature (branches of the carotid, aorta, femoral, popliteal, etc. arteries).

A stent constructed in accordance with the invention is suitable for implantation in other branching vessels of a subject. By way of example the invention has utility for implantation in the gastrointestinal system, the tracheobronchial tree, the biliary system and the genitourinary system.

From the above it is appreciated that one object of the invention is a bifurcating stent which can be expanded from an insertion to an in use configuration. This and other object advantages and features of the invention will become better understood from a detailed description of the invention which is described in conjunction with the accompanying drawings.

BEST MODE FOR PRACTICING THE INVENTION

Figure 1:
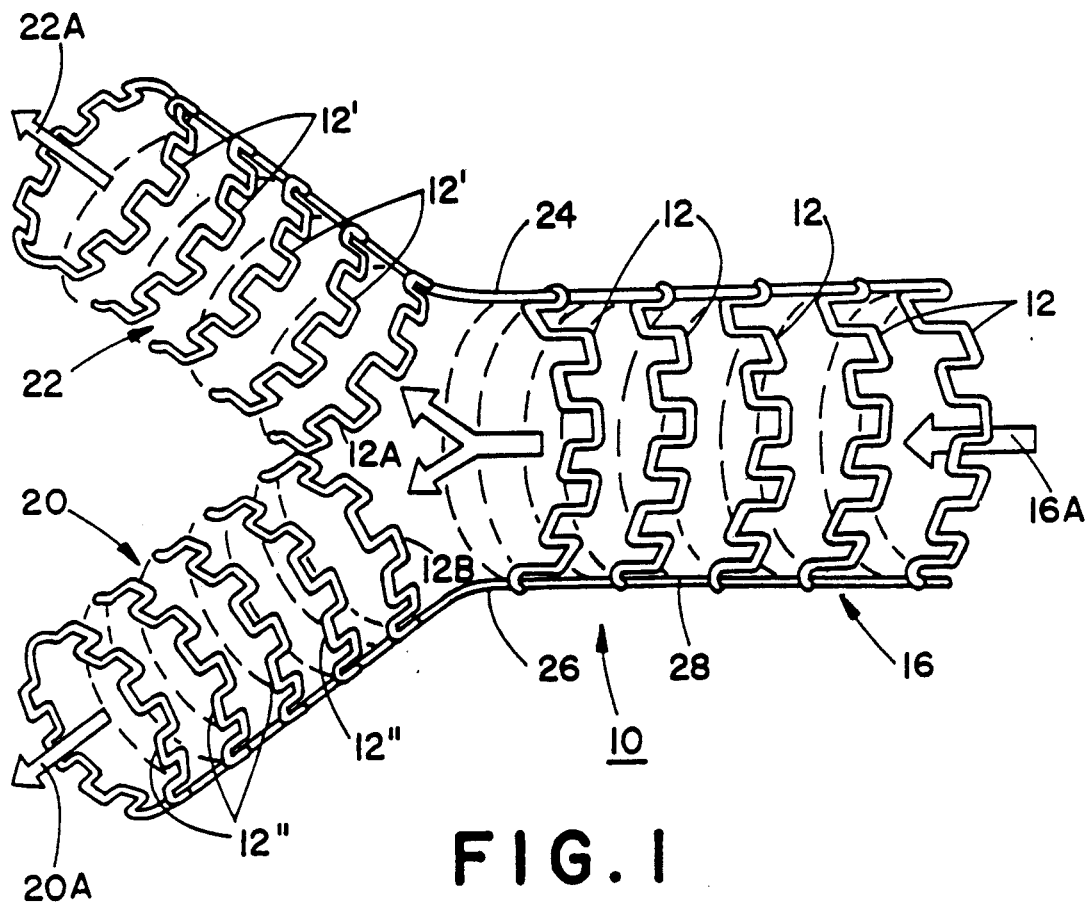
FIG. 1 is a perspective view of a bifurcating stent constructed in accordance with the invention.

Turning now to the drawings, FIG. 1 depicts a bifurcating stent 10 for implantation in a subject vessel. While the stent 10 has use in conjunction with other subject vessels, the preferred embodiment of the stent is described in conjunction with use with a blood vessel wherein the stent 10 is utilized for reinforcing the existing vascular structure.

The stent of FIG. 1 is shown in a contracted state prior to insertion within a subject. Copending patent application entitled *Endovascular Stent Apparatus and Method* which was filed Jan. 9, 1989 under application Ser. No. 07/295,129 to Hillstead discloses a technique for fabricating an in-line stent that can be expanded after it is controllably inserted within a subject by means of a balloon catheter The disclosure of this copending patent application is incorporated herein by reference.

Figure 1A:
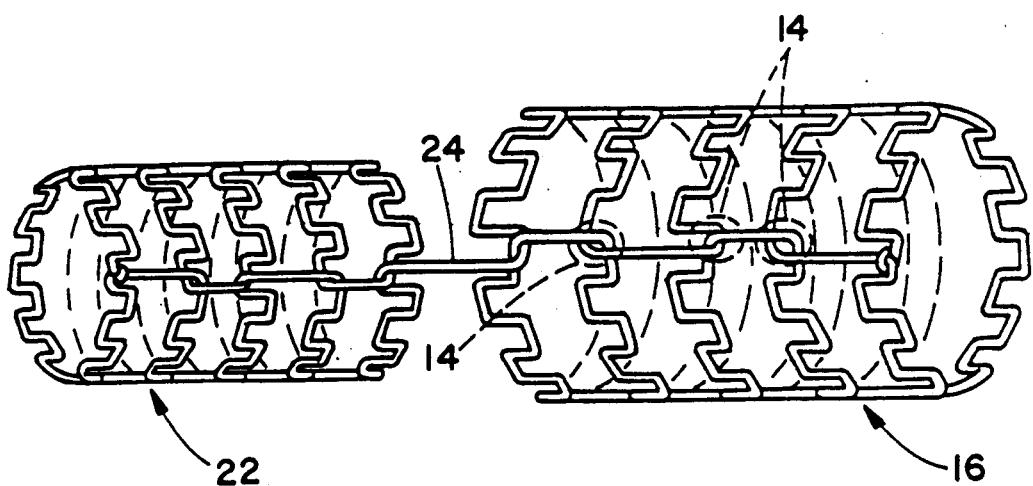
FIG. 1A is plan view of the FIG. 1 bifurcating stent illustrating a backbone structure that interconnects branch portions of the stent.

The stent 10 includes a main or trunk portion constructed from a series of generally parallel oriented loops 12 interconnected by a sequence of half-hitch connections 14 (FIG. 1A) which extend along an axial dimension. In combination the series of loops 12 form a generally cylindrical lattice or matrix 16 that defines a first flow passageway along the direction of the arrow 16A of FIG. 1.

Two additional cylindrical lattices 20, 22 having diameters less than the lattice 16 are similarly constructed from a sequence of loops interconnected by a half hitches which define flow passageways (indicated by arrows 20A, 22A in FIG. 1) extending away from the first flow passageway at angles dependent upon the vessel structure into which the stent 10 is inserted.

The lattice 16 is preferably constructed from a flexible wire 24 that connects this lattice 16 to the lattice 22. The same wire 24 forms the series of interconnected loops 12' that form the lattice 22.

A second wire 26 interconnects the cylindrical lattice 16 with the cylindrical lattice 20. The wire 26 forms a backbone 28 extending axially along the length of the lattice 16 that extends away from the lattice 16 and is used to construct the interconnecting loops 12" of the lattice 20. Appropriate bending of the portions of the wires 24, 26 interconnecting the lattices 16, 20, 22 allows the angles between flow paths to be properly oriented before the stent 10 is inserted into a vessel.

The loops 12a, 12b of the lattices 20, 22 closest to the lattice 16 are not interconnected in the preferred design. A small loop of wire could be used to interconnect these lattices 20, 22. Also, backbones similar to the backbone 28 could be added to the two lattices 20, 22.

Other techniques are known in the art for constructing cylindrical expansible forms for use in stent construction. As an additional example, U.S. Pat. application Ser. No. 240,000 entitled "Radially Expandable Endoprosthesis and the Like" discloses a stent constructed from a wire which spirals around a fluid flow path in a series of interconnected loops. A bifurcating stent which defines branching flow paths such as those depicted in FIG. 1 can also be constructed using interconnected spirally loops as disclosed in this pending patent application.

The bifurcating stent of the invention can also be constructed using a tubular passageway design similar to that disclosed in the Palmaz '665 patent. Other stent designs and a number of suitable materials can be used in constructing a bifurcating stent in accordance with the invention.

Figure 2A:
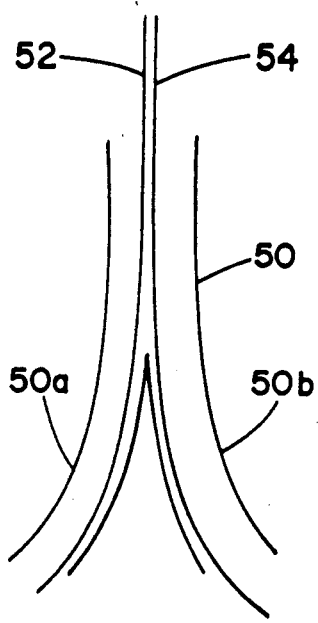
FIG. 2A is a schematic depiction of a blood vessel showing a branching juncture of that vessel with two guidewires in place.

A method of implantation for a bifurcating stent is depicted in FIGS. 2A-2F. For ease in illustration, the stent disclosed in these figures has been schematically depicted as a series of spiraling interconnected loops such as that disclosed in '000 patent application. As seen in FIG. 2A, a main trunk 50 of a blood vessel splits into two branches 50a, 50b. Two guide wires 52, 54 have been routed through a subject cardiovascular system and into the branches 50a, 50b respectively. Techniques for routing guidewires into a subject are well known in the prior art.

Once the two guidewires 52, 54 have been inserted into the position shown in FIG. 2A, a bifurcating stent 10' (FIG. 2B) is slipped over the proximal ends of the guidewires 52, 54 and routed to the branches of the blood vessel. A bifurcating stent 10 such as that depicted in FIG. 1 is suitable for implantation in the branching vessel 50 depicted in FIG. 2B. The two branching cylindrical lattices of the stent 10 are routed separately over the guidewires 52, 54 and guided with the help of a guide catheter into the subject until the FIG. 2B position of the stent 10' is achieved.

Figure 2B:
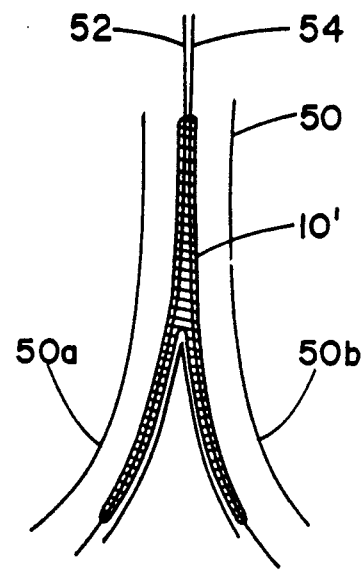
FIG. 2B shows the branching blood vessel of FIG. 2A wherein a stent constructed in accordance with the invention has been inserted.
Figure 2C:
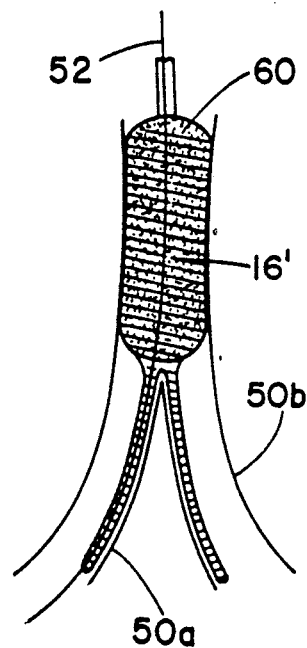
FIG. 2C shows a balloon inflated to bring a portion of a bifurcating stent into contact with inner walls of the branching blood vessel.

As seen in FIG. 2B, in the inserted configuration, the stent 10' is tightly coiled and therefore passes freely into the subject blood vessel. The stent 10' is typically inserted through a guide catheter (not shown) so that the coils or loops that form the bifurcating stent do not engage the inner walls of the blood vessel. To fix the stent 10' in place, one guidewire is removed and a balloon catheter having a distally located balloon 60 is inserted into the stent's cylindrical lattice 16' and inflated to bring the cylindrical lattice 16' into contact with the blood vessel walls. The lattice 16' engages the main trunk portion of the blood vessel so that during fabrication of the stent 10' the initial diameter of the loops that make up the lattice 16' may be chosen to be greater than the two branching lattices.

Figure 2D:
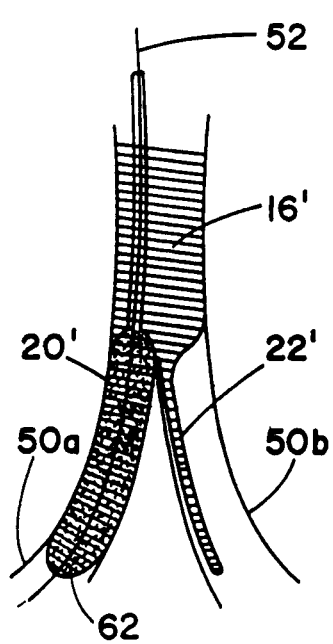
FIG. 2D shows one leg or branch of the bifurcating stent expanded into contact with one branch of the blood vessel.
Figure 2E:
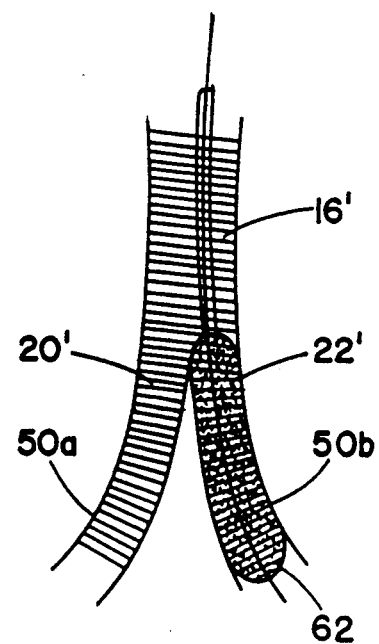
FIG. 2E shows a second branch or leg of the bifurcating stent expanded into contact with the blood vessel wall.
Figure 2F:
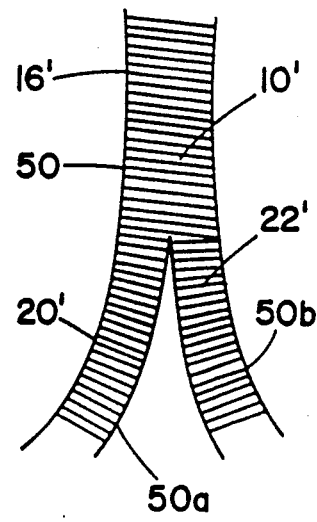
FIG. 2F shows the stent placed within the blood vessel with the balloon catheter(s) used in deploying the stent withdrawn from the blood vessel.

FIGS. 2D and 2E show a smaller dilatation balloon 62 that is routed through the expanded cylindrical lattice 10' and placed into one and then the other branch of the stent 10' over a single guidewire. When the balloon 62 is inflated the two branch lattices 20',22' of the stent expand into contact with the branching blood vessels 50a, 50b respectively. FIG. 2F shows the fully deployed branching stent 10' supporting the lumen of both the main trunk 50 and two branches 50a, 50b of the blood vessel.

Figure 3A:
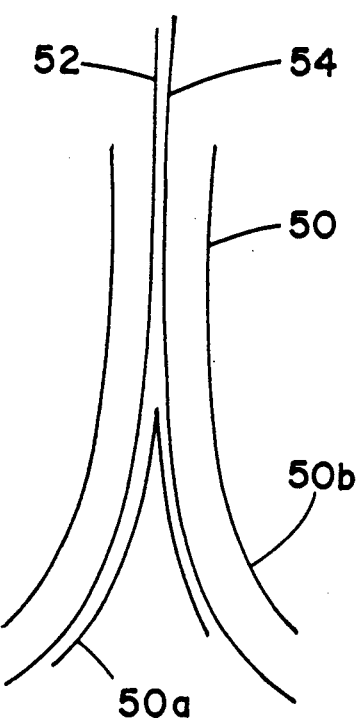
FIGS. 3A-3D show an alternate mounting technique for a bifurcating stent wherein the stent is mounted on a balloon catheter which is inflated to bring the entire stent into contact with the inner wall members of the branching vessel.
Figure 3B:
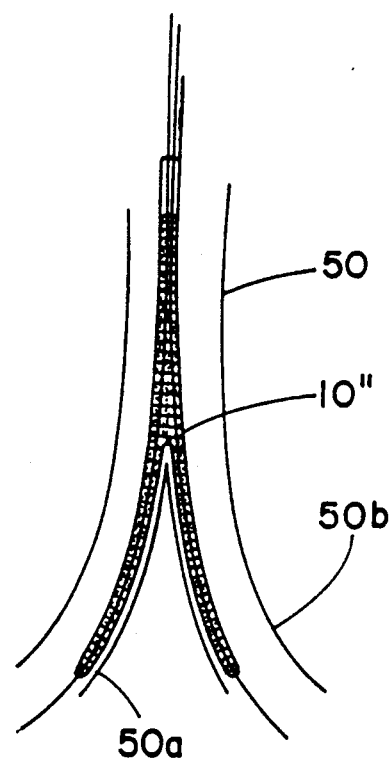
Figure 3C:
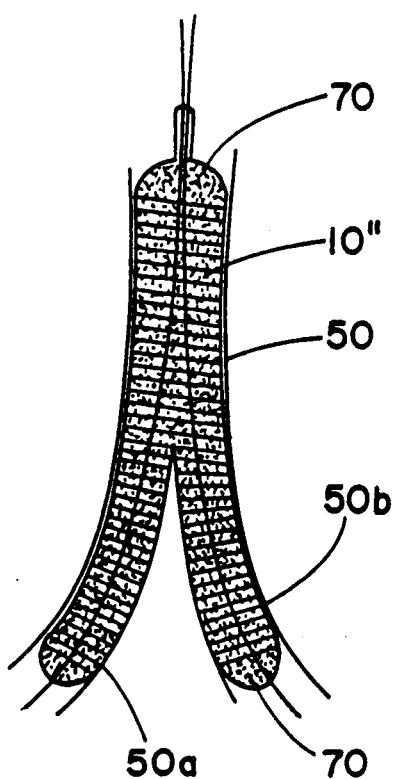
Figure 3D:
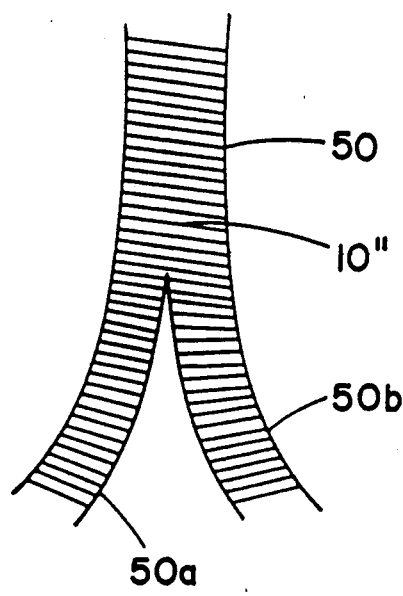

FIG. 3A shows a typical blood vessel bifurcation, again with a guidewire positioned in each of the two branches of the vessel. FIG. 3B shows a bifurcated dilatation balloon 70 over which a bifurcated stent 10" has been compressed. Two guidewires 52, 54 are used to guide the branching dilatation balloon plus the bifurcated stent into the vessel. FIG. 3C shows that the fully dilated bifurcated balloon 70 has deployed the bifurcated stent into place. FIG. 3D shows the fully deployed bifurcated stent 10" with the dilatation balloon removed.

A branching or bifurcated stent may be deployed in other ways without resort to a balloon catheter. For example, a bifurcated spring stent passed over two guidewires and contained within a guide catheter could be deployed by passing the guide catheter towards the bifurcation of the vessel, at which time the stent would be ejected into place by advancing a smaller inner catheter through the guide catheter into contact with the stent. The method of deployment of a branching stent will largely depend on the design of the stent and the success of the different deployment techniques for different branching vessel configurations.

The stent may be produced from a variety of materials, either alone or in combination, such as metals or alloys (stainless steel, titanium, tantalum, nitinol, Elgiloy, NP35N) that can vary in their springiness, malleability, and response to temperature; polymers (polyurethane, polyether sulfone, polyimide, polycarbonate, polyethylene, etc.) that can vary in their ability to bioabsorb or biodegrade; carbon; and ceramics. Various surface treatments can be applied to render the stents more biocompatible (pyrolytic carbon, hydrogels, etc.) and to provide for the elution of drugs (heparin, antiplatelet agents, platelet-derived growth factor, antibiotics, steroids, etc.).

The present invention has been described with a degree of particularity. It is the intent that the invention include all modifications and alterations from the disclosed embodiments that fall within the spirit of slope of the appended claims.

I claim:

1. A bifurcating stent for placement in a subject vessel comprising:
   a first generally cylindrical matrix of filament material forming a series of interconnected loops that define a first flow path for fluid flow; and a second generally cylindrical matrix of filament material forming a series of interconnected loops that define a second branching flow path; said first and second matrices connected by a flexible interconnecting member bent to define an angle between the first and the branching flow paths;
   said matrices constructed from a material that allows that stent to conform to an insertion configuration and expand to an in place configuration.

2. The bifurcating stent of claim 1 additionally comprising a third generally cylindrical matrix of filament material forming a series of interconnected loops that define a third flow path wherein one of the three matrices has a larger diameter to define a trunk matrix and further wherein two smaller diameter matrices are connected to the trunk matrix by flexible interconnecting members bent to define angles between the trunk matrix and the two smaller diameter matrices.

3. The bifurcating stent of claim 1 wherein adjacent loops along the length of the first and second matrices are interconnected by half hitch junction and end loops of the first and second matrices are connected by the flexible interconnecting member.

4. The bifurcating stent of claim 1 wherein the loops of both the first and the second matrix comprise a series of spiralling loops.

5. A bifurcating stent for placement in a subject vessel comprising:
   a first series of filament loops that define a first flow path for blood flow through the stent; and at least one additional series of filament loops which define a second branching flow path; said first and additional series of loops connected by a flexible interconnecting member which is bent to define an angle between the first and the branching flow paths;
   said filament loops constructed from a material that allows the stent to conform to an insertion configuration and expand to an inplace configuration in contact with inner walls of a branching vessel.

6. The stent of claim 5 wherein adjacent loops of both the first and the additional series of filament loops are interconnected by half hitch junctions.

7. The stent of claim 5 wherein the filament loops of both the first and the additional series of filament loops comprise a series of spiralling loops.

8. A method for implanting a branching stent having first and second branching portions connected together at a junction comprising the steps of:
   routing a first guidewire into a subject to a branch location and inserting the first guide wire into a first branch vessel at the branch location;
   routing a second guidewire into a subject to said branch location and inserting the second guidewire into a second branch vessel at the branch location;
   inserting the branching stent to the region of the branch location and routing the first and second branching portions of said stent into the first and second branch vessels;
   expanding the first branching portion of said stent into contact with an inner wall of one branch vessels;
   expanding the second branching portion of said stent into contact with an inner wall of a second branch vessel; and
   withdrawing the first and second guidewires, leaving said stent at the branch location.

9. The method of claim 8 wherein the step of inserting the branching stent is performed by mounting the branching stent to a bifurcating balloon located at the distal end of an insertion catheter, routing the balloon and stent to the branch location, and wherein the step of expanding the first and second branching portions is performed by inflating the bifurcating balloon to bring the stent into contact with the inner wall of the first and second branch vessel, said method including an additional step of deflating the bifurcating balloon and retracting the insertion catheter.

10. A method for implanting a branching stent having a main stent portion and first and second branching stent portions connected together at a junction comprising the steps of:

routing a first guidewire into a subject to a branch location of a main vessel and inserting the first guidewire into a first branch vessel at the branch location;

routing a second guidewire into a subject to said branch location and inserting the second guidewire into a second branch vessel at the branch location;

inserting the branching stent into the subject to a region of the branch location and routing the first and second branching portions of said stent into the first and second branch vessels leaving a main stent portion within the main vessel;

causing the stent portions to come into contact with inner walls of the vessel; and withdrawing the first and second guidewires to leave said stent at the branch location.

11. The method of claim 10 wherein the step of inserting the branching stent is performed by mounting the branching stent to a bifurcating balloon located at the distal end of an insertion catheter, routing the bifurcating balloon and branching stent to the branch location, and wherein the step of causing the stent portions to come into contact with inner walls of the vessel is performed by inflating the bifurcating balloon to bring the stent into contact with the inner walls of the vessel, said method including the additional steps of deflating the bifurcating balloon and withdrawing the insertion catheter.

12. The method of claim 10 wherein the step of causing the stent portions to come into contact with inner walls of the vessel is performed by successively routing an appropriately dimensioned balloon into the main vessel and the first and second branch vessels and inflating the balloon to expand the main, first and second branching stent portions.

13. A method for implanting a stent having a main portion and first and second branching portions connected together at a junction to form a branching stent comprising the steps of:

routing a guidewire into a subject to a branch vessel location;

inserting the branching stent to the branch vessel location by advancing the branching stent along the guidewire and inserting the first and second branching portions of said stent into first and second branch vessels leaving the main portion of the stent within a main vessel;

causing the main, first, and second branching portions of said stent to come into contact with inner walls of the branching and main vessels; and withdrawing the guidewire from the subject to leave said stent at the branch vessel location.

14. The method of claim 13 wherein the step of inserting the branching stent is performed by mounting the branching stent to a bifurcating balloon located at a distal end of an insertion catheter, routing the bifurcating balloon and branching stent into the subject, and wherein the bifurcating balloon is inflated to bring the stent into contact with inner walls of the main and the first and second branch vessels, said method including the additional steps of deflating the balloon and withdrawing the insertion catheter.

15. The method of claim 13 wherein the step of causing the main, first, and second branching portions to come into contact with inner walls of the vessels is performed by sequentially routing an appropriately dimensioned dilation balloon into the main, first and second branching portions of the stent and inflating the balloon to expand the main, first and second branching portions.

16. The method of claim 13 wherein as the branching stent is inserted it is in a contracted configuration and wherein the stent is expanded to bring it into contact with the inner walls of the main and branch vessels.

* * * * *